(12) United States Patent
Michaeli (10) Patent No.: US 7,471,761 B2
(45) Date of Patent: Dec. 30, 2008

(54) SYSTEM AND METHOD FOR COMPUTING ORAL BONE MINERAL DENSITY WITH A PANORAMIC X-RAY SYSTEM

(75) Inventor: Daniel Michaeli, Bronx, NY (US)

(73) Assignee: Schick Technologies, Inc., Long Island City, NY (US)

( * ) Notice: Subject to any disclaimer, the term of this patent is extended or adjusted under 35 U.S.C. 154(b) by 0 days.

(21) Appl. No.: 11/228,132

(22) Filed: Sep. 15, 2005

(65) Prior Publication Data

US 2007/0058786 A1 Mar. 15, 2007

(51) Int. Cl.
*A61B 6/14* (2006.01)
(52) U.S. Cl. .......................... 378/38; 378/39
(58) Field of Classification Search ............. 378/38–40, 378/207; 433/29
See application file for complete search history.

(56) References Cited

U.S. PATENT DOCUMENTS

| | | | | |
|---|---|---|---|---|
| 5,267,293 | A * | 11/1993 | Virta | 378/40 |
| 5,335,260 | A | 8/1994 | Arnold | 378/207 |
| 5,386,448 | A | 1/1995 | Tammisalo et al. | 378/38 |
| 5,784,429 | A * | 7/1998 | Arai | 378/38 |
| 5,852,647 | A * | 12/1998 | Schick et al. | 378/53 |
| 5,898,753 | A | 4/1999 | Schick et al. | 378/54 |
| 5,912,942 | A | 6/1999 | Schick et al. | 378/98.8 |
| 5,995,583 | A | 11/1999 | Schick et al. | 378/38 |
| 6,069,935 | A | 5/2000 | Schick et al. | 378/98.8 |
| 6,224,373 | B1 | 5/2001 | Lee et al. | 433/172 |
| 6,320,931 | B1 | 11/2001 | Arnold | 378/56 |
| 6,381,301 | B1 | 4/2002 | Massie | 378/39 |
| 6,909,771 | B2 * | 6/2005 | Waggener et al. | 378/54 |
| 7,095,905 | B1 * | 8/2006 | Peterson | 382/284 |
| 2001/0048733 | A1 * | 12/2001 | Schulze-Ganzlin | 378/62 |
| 2002/0067798 | A1 * | 6/2002 | Lang | 378/54 |
| 2002/0094951 | A1 | 7/2002 | Horiuchi et al. | 514/12 |

(Continued)

FOREIGN PATENT DOCUMENTS

RU 2 134 064 C1 8/1999

(Continued)

OTHER PUBLICATIONS

Steven R. Cummings et al., "Clinical Use of Bone Densitometry", Journal of American Medical Association, vol. 288, No. 15, pp. 1889-1897, Oct. 16, 2002.

(Continued)

*Primary Examiner*—Edward J Glick
*Assistant Examiner*—Anastasia Midkiff
(74) *Attorney, Agent, or Firm*—Fitzpatrick, Cella, Harper & Scinto (57) ABSTRACT

A method of computing oral bone mineral density using a panoramic x-ray system. A reference phantom having a known density is provided. A digital panoramic image of a body part and the reference phantom is obtained by irradiating the body part and the reference phantom. The reference phantom is disposed in a location free from anatomical features and in the same scan line as the body part. A relationship is established between a region of the image corresponding to a portion of the body part and a region of the image corresponding to the reference phantom. Bone mineral density is calculated based upon the established relationship and the known density of the reference phantom.

7 Claims, 6 Drawing Sheets

U.S. PATENT DOCUMENTS

| | | | |
|---|---|---|---|
| 2002/0114425 A1* | 8/2002 | Lang et al. | 378/56 |
| 2003/0015208 A1 | 1/2003 | Lang et al. | 128/922 |
| 2003/0023167 A1 | 1/2003 | Azzam et al. | 600/449 |
| 2003/0031292 A1 | 2/2003 | Lang | 378/54 |
| 2003/0058989 A1* | 3/2003 | Rotondo et al. | 378/40 |
| 2003/0063704 A1 | 4/2003 | Lang | 378/54 |
| 2003/0112921 A1* | 6/2003 | Lang et al. | 378/54 |
| 2003/0138076 A1* | 7/2003 | Massie | 378/39 |
| 2004/0062358 A1* | 4/2004 | Lang et al. | 378/207 |
| 2004/0081287 A1* | 4/2004 | Lang et al. | 378/210 |
| 2004/0114726 A1* | 6/2004 | Lee et al. | 378/207 |
| 2005/0010106 A1* | 1/2005 | Lang et al | 600/425 |
| 2005/0078802 A1* | 4/2005 | Lang et al. | 378/207 |
| 2005/0226374 A1* | 10/2005 | Lang et al. | 378/54 |
| 2008/0063139 A1* | 3/2008 | Pantsar et al. | 378/40 |

FOREIGN PATENT DOCUMENTS

| | | |
|---|---|---|
| WO | WO 03/049615 A1 | 6/2003 |

OTHER PUBLICATIONS

E. Nagourney, "When Teeth Tell Tales on Bones", New York Times, p. F6, Dec. 7, 2004.

A. Taguchi et al., "Validation of Dental Panoramic Radiography Measures for Identifying Postmenopausal Women with Spinal Osteoporosis", American Journal Roentgenology, vol. 183, pp. 1755-1760, Dec. 2004.

E. Siris et al., "Identification and Fracture Outcomes of Undiagnosed Low Bone Mineral Density in Postmenopausal Women", Journal of American Medical Association, vol. 286, No. 22, pp. 2815-2822, Dec. 12, 2001.

J.A. Kanis et al., "The Diagnosis of Osteoporosis", Journal of Bone and Mineral Research, vol. 9, No. 8, pp. 1137-1141, Aug. 1994.

K. Horner et al., "Mandibular Bone Mineral Density as a Predictor of Osteoporosis", British Journal of Radiology, vol. 69, No. 827, pp. 1019-1025, Nov. 1996.

W. Pluskiewicz et al., "Mandibular Bone Mineral Density Measured Using Dual-Energy X-Ray Absorptiometry: Relationship to Hip Bone Mineral Density and Quantitative Ultrasound at Calcaneus and Hand Phalanges", British Journal of Radiology, vol. 73, pp. 288-292, Mar. 2000.

N. Von Wowern et al., "Bone Mineral Content by Photon Absorptiometry of the Mandible Compared with that of the Forearm and the Lumbar Spine", Calcified Tissue Int., vol. 42, No. 3, pp. 157-161, Mar. 1988.

* cited by examiner

SYSTEM AND METHOD FOR COMPUTING ORAL BONE MINERAL DENSITY WITH A PANORAMIC X-RAY SYSTEM

BACKGROUND OF THE INVENTION

1. Field of the Invention

This invention relates generally to the field of assessing bone mineral density, and more particularly to assessing oral bone mineral density using a panoramic x-ray system and a reference phantom.

2. Related Art

Bone mineral density (BMD, $g/cm^2$) is widely used by doctors and physicians in detecting and managing osteoporosis and in predicting fracture, particularly in higher-risk patients such as postmenopausal women. Osteoporosis is a disease in which the bones become extremely porous and fragile, are subject to fracture, and heal slowly and often poorly. This disease occurs especially in women following menopause and often leads to curvature of the spine from vertebral collapse. The thinning of the bones with a reduction in bone mass is generally due to a depletion of calcium. Left unchecked, osteoporosis can lead to changes in posture, physical abnormality (for example, a hunched back), and decreased mobility. Early diagnosis of osteoporosis is critical and treatments have been shown to slow progressive bone loss and reduce the risk of fracture. Such treatments include calcium supplementation, hormone replacement therapy, and the use of bisphosphonates (a class of drugs used to strengthen bone) and intermittent parathyroid hormone (a hormone critical to calcium and phosphorus balance).

BMD is believed to be the single best predictor of fracture in asymptomatic postmenopausal women. (See, e.g., J. A. Kanis et al., "The Diagnosis of Osteoporosis," J Bone and Mineral Res. 1994; 9:1137-1141.) While densitometry of the hip and spine has become the so-called "gold-standard" for assessing the risk of fracture, a variety of peripheral sites, such as the finger, are also utilized and have been found to be predictive of future fracture in large prospective trials. See, e.g., S. Miller et al., "Identification and Fracture Outcomes of Undiagnosed Low Bone Mineral Density in Postmenopausal Women," JAMA 2001; 286(22): 2815-2821; also see, e.g., U.S. Pat. No. 5,852,647 (Schick, et al.), U.S. Pat. No. 5,898,753 (Schick, et. al.), U.S. Pat. No. 5,912,942 (Schick, et al.), and U.S. Pat. No. 6,069,935 (Schick, et al.).

Measuring BMD may be particularly interesting to practitioners in the dental industry for a variety of reasons. First, similar to other peripheral sites, it appears that oral BMD is related to systemic BMD, and therefore can also be a reliable predictor of osteoporosis. Dentists tend to see their patients often, typically performing x-ray examinations every 6-12 months, which is a greater regularity than that with which general and other physicians see many of their patients. The dentists' office, therefore, can be an excellent place for routine BMD tests to occur, and there is a need for an in-office tool that a dentist can use to take such tests.

Furthermore, a measurement of oral BMD may prove beneficial in the diagnosis of periodontal disease, which is a bacterial infection that can destroy the attachment fibers and supporting bone that hold the teeth in the mouth. Such a bacterial infection typically causes the loss of soft tissue attachment and the resorption of alveolar bone (the jaw section containing the tooth sockets). Resorption is the process of losing substance, as bone, when it is remodeled or reshaped, undergoes both new formation and resorption. The loss of soft tissue attachment and the resorption of alveolar bone may result in tooth loss, edentulousness, and resorption of the remaining residual ridge, which in turn can lead to a further loss of oral bone.

There is therefore a great need for an in-office tool for measuring oral BMD so that dental practitioners such as periodontists, who are concerned with prevention, diagnosis, and treatment of diseases affecting the gums and supporting structures of the teeth, could potentially stage the progression of disease in the mouth and make better treatment decisions.

BMD measurements are also commonly used in connection with tooth implant surgery. In particular, tooth implant surgery is commonly preceded by a measure of BMD by quantitative computed tomography (described in more detail below) or cone beam tomography to ensure that the mouth has sufficient integrity to support the operation. Of course, BMD measurements are useful in other applications as well.

Conventional central and peripheral densitometry techniques are understood by those having ordinary skill in the art. Most commercially available methods for BMD measurement pass a low-intensity beam of x-rays through a patient, and a radiation detector on the other side measures how much of the beam is absorbed. Part of the beam is absorbed by the bone and part by the surrounding soft tissue, and each technique measures these differently. Generally, such techniques involve an energy source of either single or dual energy. Whereas early densitometry devices utilized radiologic isotopes as the energy source, over time these were replaced with more stable and sophisticated x-ray generators.

Known techniques include single energy x-ray absorptiometry (SXA), radiographic absorptiometry (RA), computed tomography (CT), quantitative computed tomography (QCT), and dual-energy x-ray absorptometry (DEXA). SXA computes bone mineral from the increased absorption of the beam as it passes through soft tissue and bone. RA measures BMD in extremities such as the fingers relative to an aluminum calibration wedge on the film. CT utilizes an array of detectors to collect x-ray attenuation data from x-rays that pass through the body. The data are input as digital data into a computer, which processes that data and reconstructs planar cross-sectional images of the internal structures of the body through which x-rays pass. QCT requires the use of a bone-equivalent calibration phantom which is scanned simultaneously with the patient to provide BMD measurements in axial images. The planar images can be further reconstructed into three-dimensional voxels and QCT is the only known technique for computing true three-dimensional density. DEXA uses a dual energy approach, and in particular, uses two planar x-ray images obtained using x-rays with different energy levels to compensate for tissue variations and quantify bone mass in an x-ray image. Typical existing DEXA systems rely on known x-ray absorption characteristics of hard tissue and soft tissue to both high-energy and low-energy radiation, thereby enabling existing DEXA systems to determine the hard tissue mass.

Densitometry techniques known in the art include both film and digital-based techniques. Generally, an x-ray filter separates the energy spectra and a reference standard is included to correlate x-ray attenuation to BMD. An example is provided in U.S. Pat. No. 5,335,260 (Arnold), which utilizes a calibration phantom representative of human tissue containing variable concentrations of calcium. The calibration phantom serves as a calibration reference for quantifying calcium, bone mass and bone mineral density in radiography and CT imaging systems.

The general principles discussed above have been applied to measure a variety of anatomic sites, including oral structures. U.S. Patent Application Publication No. US 2002/

0114425 A1 (Lang et al.), for example, discusses the measurement of oral BMD from a dental x-ray image which includes using a calibration phantom and a software algorithm to relate pixel intensity to measures of bone mineral density and/or architecture.

Dental imaging can be generally segmented into either intra-oral or extra-oral modalities. In intra-oral imaging, an electronic sensor is located inside the mouth, whereas in extra-oral imaging, the sensor is located outside the mouth. Intra-oral techniques are generally less ideal for densitometry, since the so-called source-to-target distance is not typically fixed. Moreover, in intra-oral imaging, the dental x-ray tube generally maintains the freedom to rotate in multiple planes, which may lead to an inaccurate or imprecise assessment. Further, fashioning a reference phantom small enough to be suitable for the mouth is challenging. Although there may be ways of attempting to control these variables, utilizing this technique in a clinical environment may be challenging and therefore it is preferable to altogether remove these potential error sources.

Extra-oral examinations may be better suited for densitometric assessment since, with the detector outside the mouth, the evaluation is more controllable and may be more comfortable for the patient. In particular, whereas in intra-oral imaging a reference standard would need to be included in the mouth and over the detector, in extra-oral imaging there would be more flexibility of placement. Furthermore, in extra-oral imaging the clinician will generally have more freedom to analyze the particular anatomic region of interest. U.S. Pat. No. 6,381,301 (Massie) discusses a tomographic system for determining bone mineral density of a patient's mouth. Unfortunately, a drawback to this system is that few dentists have systems with tomographic capability within their practice, and therefore this technique does not provide a practical commercial tool. Standard panoramic dental x-ray systems are much more common and allow a complete view of the patient's anatomy. Panoramic measurements of mandibular inferior cortical shape and width, for instance, have been proposed as a potentially useful tool for screening spinal osteoporosis. These geometric measures are, however, an indirect index of bone mineral density.

There exists therefore a need for a fresh approach which provides a more practical tool for enabling dental practitioners to assess BMD for the purpose of treating their patients. Such a tool should be flexible, easy to use, and should capitalize on equipment that is typically found in most dental offices.

SUMMARY OF THE INVENTION

Accordingly, it is an object of the present invention to provide a practical tool for measuring oral BMD so that periodontists, who are concerned with the prevention, diagnosis, and treatment of diseases affecting the gums and supporting structures of the teeth, could potentially stage the progression of disease in the mouth and make better treatment decisions. It is also an object of the present invention to provide an inexpensive, low-radiation in-office measurement technique for this application. As digital x-ray imaging is becoming more and more prevalent within dental offices, such technique can afford an effective platform for allowing professionals to obtain useful densitometric information.

The present invention provides a system and method of computing oral BMD using a panoramic dental x-ray system and a reference phantom.

In one embodiment, the present invention provides a method of computing oral bone mineral density using a panoramic x-ray system. A reference phantom having a known density is provided. A digital panoramic image of a body part and the reference phantom is obtained by irradiating the body part and the reference phantom. The reference phantom is disposed in a location free from anatomical features and in the same scan line as the body part. A relationship is established between a region of the image corresponding to a portion of the body part and a region of the image corresponding to the reference phantom. Bone mineral density is calculated based upon the established relationship and the known density of the reference phantom. The step of obtaining a digital panoramic image of a body part may be accomplished utilizing a digital sensor, or may be accomplished by exposing film and scanning the film to obtain the digital panoramic image.

In another embodiment, the present invention provides a method of computing oral bone mineral density using a panoramic x-ray system. A reference phantom having a known density is provided. A digital panoramic image of a body part and the reference phantom is obtained by irradiating the body part and the reference phantom. The reference phantom is disposed in a location free from anatomical features and in a same scan line as the body part. A relationship is established between the known density of the reference phantom and a region of the panoramic image corresponding to the reference phantom. The established relationship is applied to a region of the panoramic image corresponding to at least a portion of the body part to calculate the bone mineral density of the body part.

BRIEF DESCRIPTION OF THE DRAWINGS

The invention will be more clearly understood by reference to the following detailed description of exemplary embodiments in conjunction with the accompanying drawings, in which.

The invention will next be described in connection with certain exemplary embodiments; however, it should be clear to those skilled in the art that various modifications, additions, and subtractions can be made without departing from the spirit or scope of the claims.

DETAILED DESCRIPTION OF THE INVENTION

The present invention provides a system and method of computing oral BMD using a panoramic dental x-ray system and a reference phantom. Among the novelties of the present invention is using a panoramic x-ray system towards this end. The capability to perform panoramic x-ray examinations is becoming more and more prevalent in dental offices, and offers an important advantage in this application, as the source-to-detector distance and x-ray tube angulation is typically fixed. Furthermore, panoramic systems are generally provided with positioning means to standardize the location of the patient's head within the imaging layer.

Before describing the present invention in detail, it is to be understood that the practice of the present invention employs, unless otherwise indicated, conventional methods of panoramic x-ray imaging and processing as known by those having ordinary skill in the art. The present invention is not limited to particular formulations or process parameters as such may, of course, vary.

Panoramic imaging is extensively utilized by dentists and oral surgeons. In one known single-energy procedure, for example, panoramic or wide angle x-ray images are produced by generating a narrow linear x-ray beam which is revolved during the exposure about an axis of rotation which passes through the anatomical structures to be examined. The x-ray tube generates x-rays at a small fixed point on an anode. Radiation generated at this point is collimated by a first slit which is parallel to the axis of rotation, passes through the patient's head and then passes through a second similar collimating slit situated in front of a screened film cassette or digital sensor which is rotated in synchronism with the rotational movement of the x-ray beam. The tube and detector motion causes the x-ray beam to sweep across the intervening anatomical structures. Both film-based and digital sensors are used in such systems, which produce a panoramic image of curved anatomical structures in the patient's head such as the mandible or maxilla.

Figure 1:
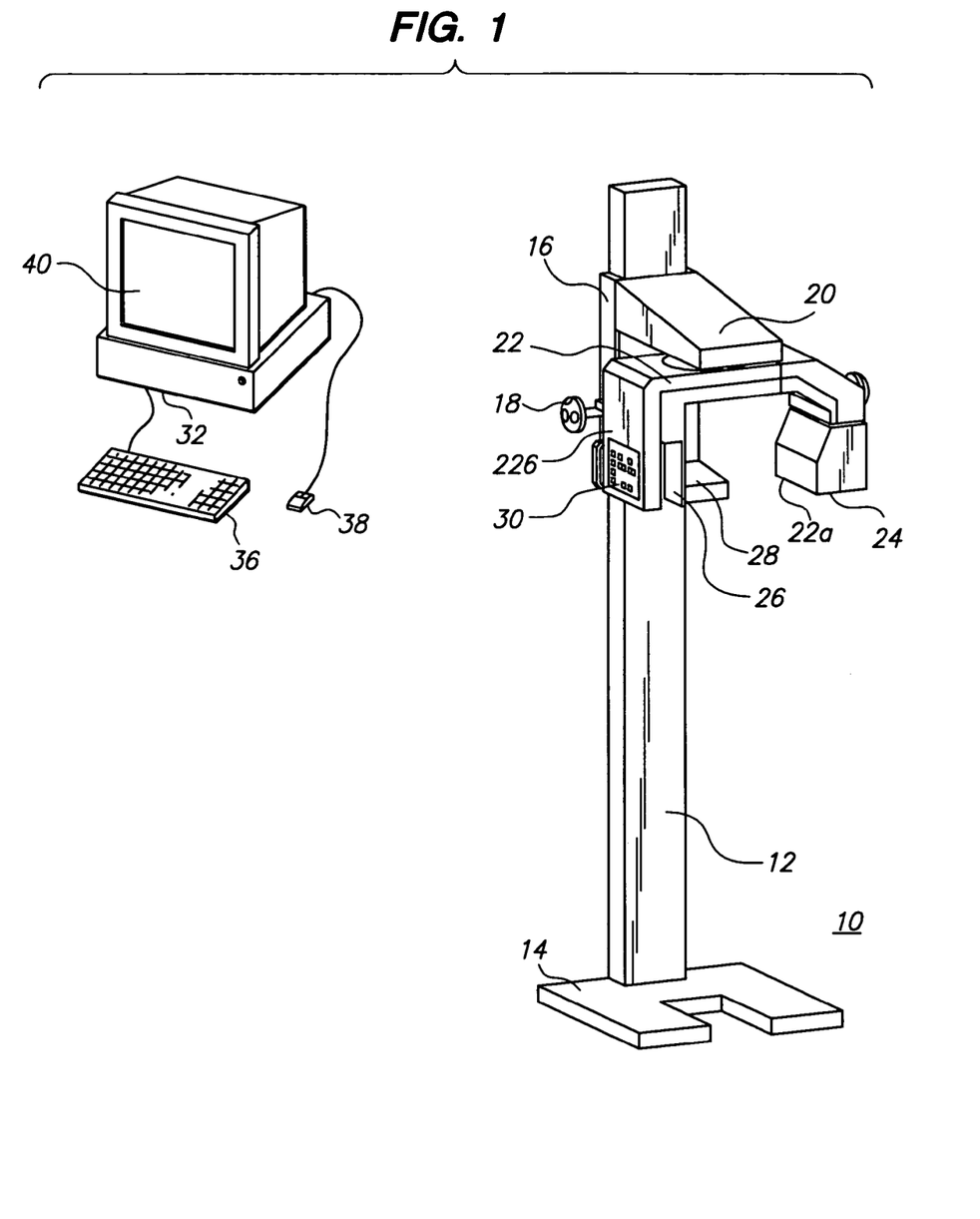
FIGS. 1 and 2 illustrate physical aspects of a panoramic x-ray imaging apparatus for use with the present invention.
Figure 2:
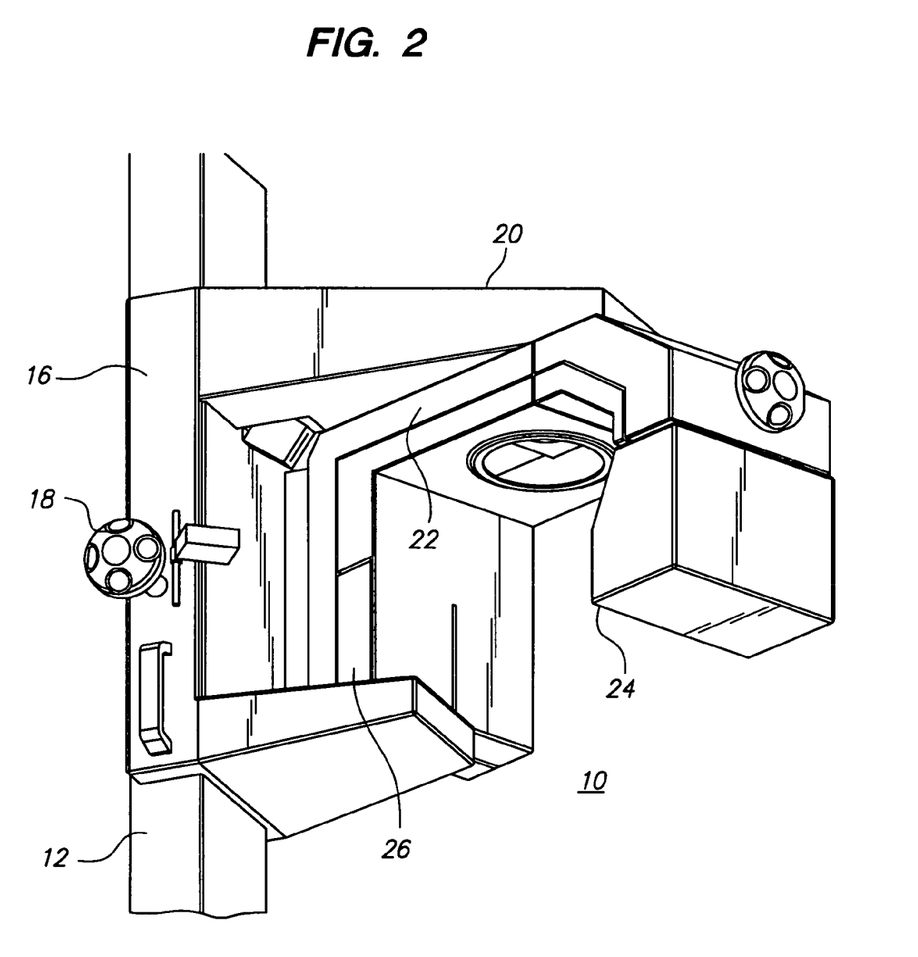

As will be explained in further detail below, the invention in one embodiment utilizes an x-ray tube, a reference standard, a receptor, positioning means, and computer software to reliably compute the BMD of a specified region of interest. FIG. 1 shows a panoramic x-ray imaging apparatus 10 for use with the present invention, in which a support column 12 stands on a base 14 of the apparatus 10. A vertical support 16 is provided for the support column 12 so as to be slidable up and down via knob 18, and a vertical carriage 20 extends from the vertical support 16. A rotary arm 22 is rotatably attached to the vertical carriage 20, and is provided with a rotary mechanism for rotating itself against the vertical carriage 20 (see, e.g., FIG. 2) by a step motor or the like.

An x-ray source 24, provided with an x-ray tube, is disposed on one end 22a of the rotary arm 22 and an x-ray receptor 26 is disposed on the other end 22b. A chin support 28 is provided, along with other positioning elements, to support and position the patient's head. The other positioning elements may include light identification means and a headrest, as well as other positioning elements which are well-known among those having ordinary skill in the art. The main purpose of the positioning elements is to align the patient correctly within the focal trough. The practitioner uses the apparatus control panel 30 in operating the panoramic x-ray apparatus 10, in which the control panel 30 includes a number of switches for performing various functions such as turning on and off the electric current source and controlling movement of the rotary arm 22.

The x-ray detector or receiver 26 may be x-ray film, stored phosphor, or a digital sensor. Solid-state sensors which convert x-rays into an electrical signal have increasingly begun to be used in place of photographic film, and such filmless radiography systems offer many advantages over traditional film-based radiography. For example, the image of the anatomy may be generated by a computer almost instantaneously, thus improving workflow and eliminating the entire film development process, including the use of potentially harmful chemicals. In addition, because the images are generated electronically, they can be easily stored in and accessed from a computer database.

Digital sensors may be wired or wireless. In digital x-ray imaging, an x-ray beam is projected from an energy source towards an electronic sensor. The x-rays impinge on the electronic sensor, which converts the x-rays into an electrical signal. The electrical signal is then transmitted to a computer, and the computer then processes the signal to produce an image on an associated output device, such as a monitor or a printer. The electronic sensor may include a charge-coupled device (CCD), a CMOS active pixel sensor (APS) array, storage phosphor device, or another type of filmless radiation sensor. A computer 32 allows the user to control the operation of the system, and to view and analyze the dental images that the system creates.

A feature of the present invention is a reference phantom, shaped in a preferred geometry. The reference phantom is constructed of materials that replicate the x-ray attenuation profile of the involved tissues, for example the x-ray attenuation characteristics of bone and soft tissue (these materials are well known in the art and will be explained in more detail below). To compute a quantitative measure of BMD, the reference phantom should be included within the field of view. A phantom of known densities allows a relationship between pixel value and equivalent BMD to be developed. This relationship is used to generate the bone mineral density of a particular region of interest.

Figure 3:
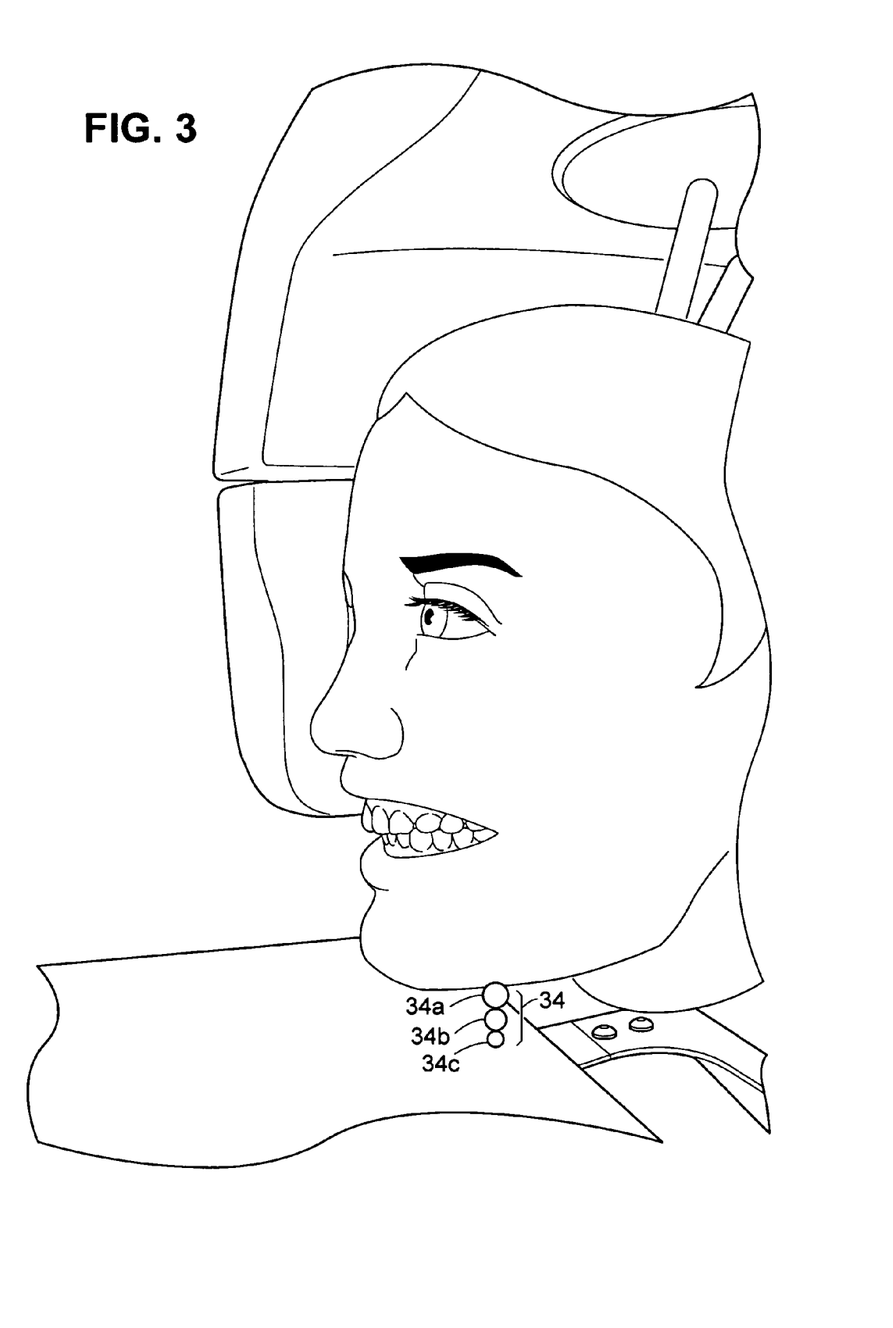
FIGS. 3 and 4 illustrate a spherical reference phantom and its positioning according to a preferred embodiment of the present invention.

In one embodiment of the present invention, spherical shapes for the reference phantom are used. Such shapes tend to reduce errors associated with the varying x-ray angle of incidence since transmission through a sphere is the same in each direction. FIG. 3 depicts phantom 34 according to the present invention. In the embodiment shown in FIG. 3, the phantom comprises three aluminum spheres or balls 34a-34c, which enables an empirical relationship between attenuation and bone mineral density to be formulated. It is noted that in FIG. 3, sphere 34a is larger in diameter than sphere 34b, which in turn is larger in diameter than sphere 34c.

It should be understood that although three spheres are shown in FIG. 3, the invention is not limited to this embodiment and other numbers of spheres could be used. In essence, enough spheres are needed to formulate a reasonable linear relationship between attenuation and BMD. As noted herein, the spheres should be placed in the scan line and plane of the region of interest, and in an area not disturbed by other tissues.

The dimensions of the spheres should be carefully selected in order to generate bone mineral densities that are in the range of the bone mineral density of the patient's mandible. From the existing literature on the topic of bone mineral density, it is known that the bone mineral density of people in general ranges from approximately 0.85 $g/cm^2$ to approximately 1.5 $g/cm^2$. The dimensions of the spheres according to one exemplary embodiment are 0.312 inches in diameter for sphere 34a, 0.250 inches in diameter for sphere 34b, and 0.187 inches in diameter for sphere 34c. Of course, although the inventors have found this range to be optimal, the present invention is not limited to these specific dimensions or this range, and the range can be expanded as needed.

Figure 4:
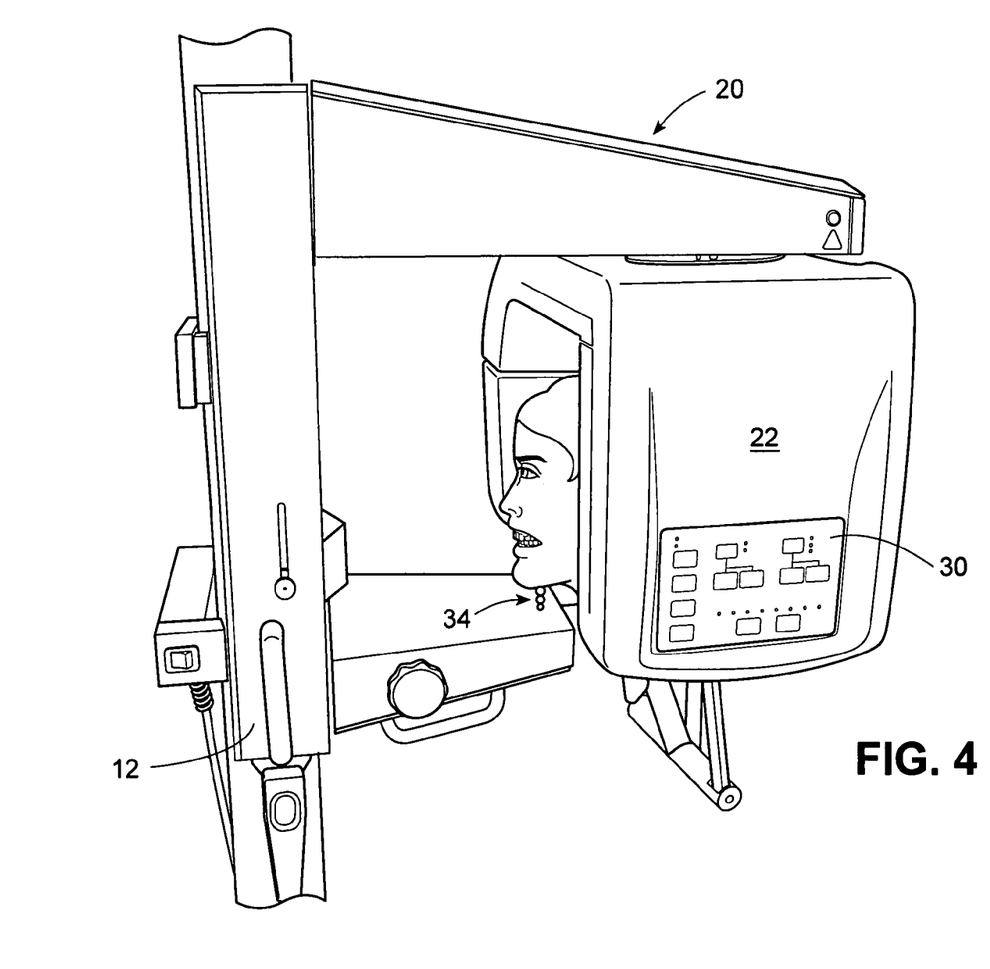

FIG. 3 also shows positioning of the phantom 34 in reference to the patient according to a preferred embodiment of the present invention. FIG. 4 is a perspective view of the same phantom 34 and the positioning thereof as shown in FIG. 3, though the view in FIG. 4 is from a longer distance in order to show how the patient is situated in reference to the panoramic x-ray machine 10 in this example. Of course, FIGS. 3 and 4 are meant to be illustrative and are by no means limiting.

In the example shown in FIGS. 3 and 4, the phantom 34 is placed adjacent to and lower than the patient's mandible. As can be seen from the figure, the spheres are preferably placed in a location devoid of human bone and soft tissue, but also a location that would be included within a panoramic examination. To obtain an accurate measure of the associated x-ray attenuation, the phantom 34 should not overlie the patient's anatomical functions. Because the x-ray energy varies depending upon the scan line, the phantom should be placed in the same area or line as the region of interest. That is, the phantom should be placed in the proper plane and without overlying any anatomy, but also in the same plane as the structure that is being imaged. In one embodiment, the balls are placed below the jaw in a scan line approximating the location of the mental foramen. While other anatomical regions would be apparent, the BMD of the mental foramen has been shown to be a particularly relevant region of interest.

In another embodiment, a material of known density could be placed beneath the entirety of the region intersecting the patient's chin and the panoramic machine's imaging layer, such that every scan line included a material of known density. Of course, the material would need to be manufactured from a low density material that created minimum scatter artifact, such as a plastic. This technique may also be used in conjunction with the aforementioned method so that a relative measure of attenuation could be ascertained for each scan line, and a complete relationship between attenuation and bone mineral density applied from a particular scan line could be obtained.

As noted, the phantom could be placed in various locations (such as below the patient's chin) as long as it is within the exposed area and is included within the same scan line as the anatomic region of interest. This matter can be of particular importance since the motion profile of panoramic x-ray systems is known to be variable; that is, the speed of the gantry as it encircles the patient is slower as the x-ray tube is firing through the anterior part of the face and cervical spine than it is at other times.

Figure 5:
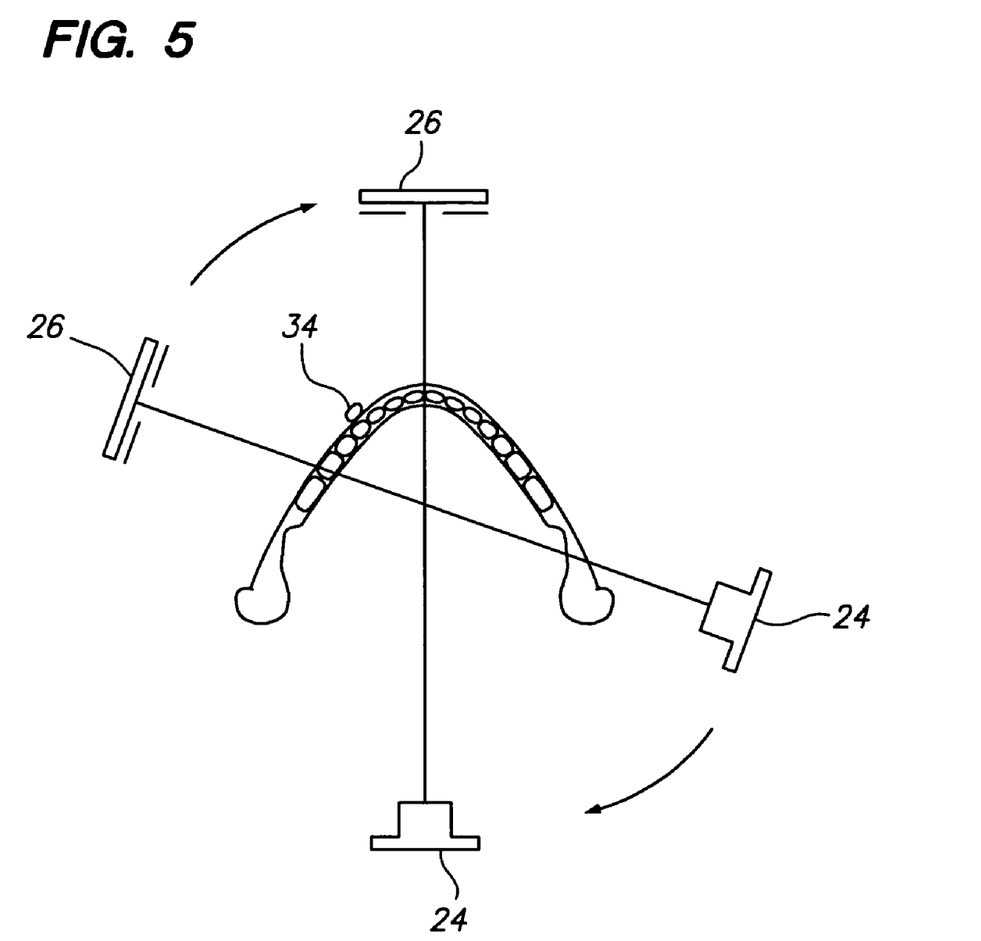
FIG. 5 shows the panoramic movement of an x-ray source and an x-ray receiver such that the mandible and the spherical reference phantom are imaged according to an embodiment of the present invention.

FIG. 5 shows the panoramic movement of the x-ray source 24 and the x-ray receiver 26 such that the mandible and the phantom 34 are imaged. The x-ray source 24 typically rotates on the mechanical assembly that encircles the patient's head to generate a series of projections representative of the oral cavity. According to a preferred embodiment of the present invention, BMD is computed by forming a relationship between the pixel values in the region of interest and a representative portion of the phantom within the present scan line. In essence, since the equivalent density of the phantom is known, a linear relationship can be formulated. Because attenuation in a panoramic examination is extremely sensitive to an object's position in the focal trough, the phantom is preferably included in each examination. A change in patient positioning, for instance, could significantly affect the relationship between pixel value and BMD, and therefore the relationship from a prior examination may not be generally applied to the present examination.

Figure 6:
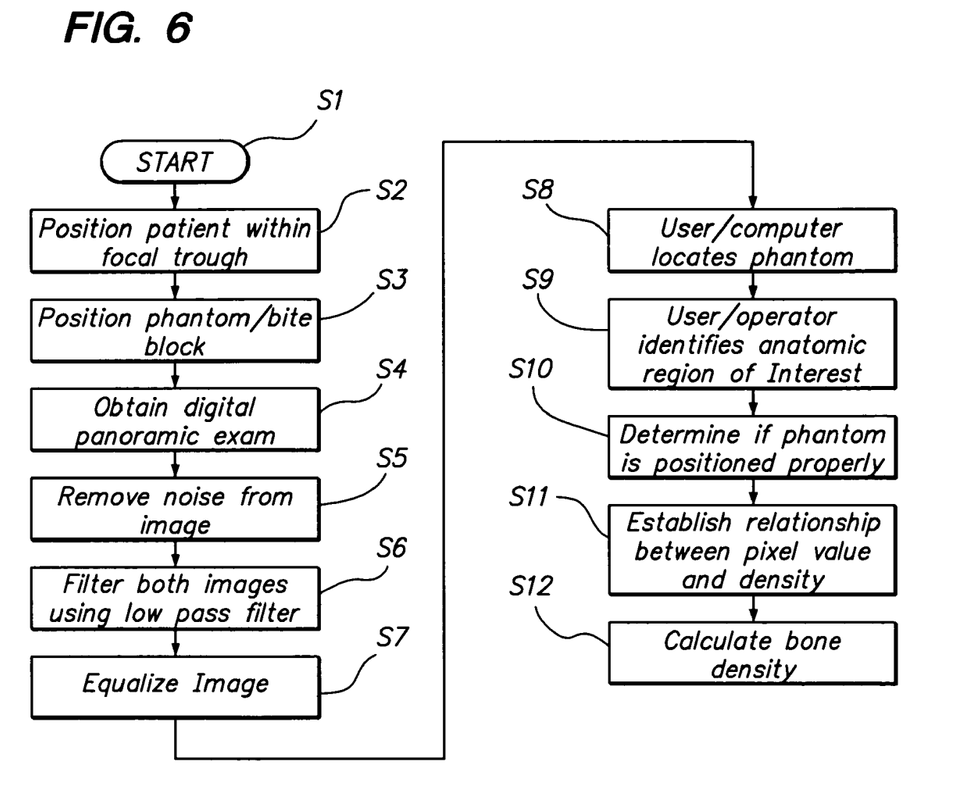
FIG. 6 is a flowchart showing a method of calculating BMD according to a preferred embodiment of the present invention.

FIG. 6 is a flowchart showing a method of calculating the BMD according to a preferred embodiment of the present invention. The process begins in step S1, and in step S2 the practitioner positions the patient within the focal trough of the panoramic x-ray machine in a way suitable for practicing the present invention, for example as shown in FIG. 4. Next, in step S3, the practitioner positions the phantom with respect to the patient's mandible and the scan line of the x-ray beam as explained herein, e.g., in a location with no other anatomy.

In step S4 the panoramic x-ray scanning begins and a panoramic examination (digital in this embodiment) is performed. According to this embodiment, different from standard panoramic x-ray techniques, the panoramic examination scans a view of the patient's entire face including the reference phantom that is placed in a location with no other anatomy as explained above. The spheres should of course not be obstructed by other anatomy since that would tend to result in an unreliable indication of their density contribution. In a preferred embodiment, the spheres are located underneath the patient's chin. In this case, the positioning of the patient's head would be higher in the field of view than normal to allow for the spheres placement. The overall goal in patient placement should be to obtain a reliable, low-artifact panoramic image where the phantom and anatomic region of interest attenuation is clear. Depending upon the exact specifications of the image layer, a second examination may be required if a standard panoramic image is necessary since in some devices, the offset of the patient's face could create artifact in distant regions of the image. In the case where an electronic sensor is utilized, a digital panoramic image is directly obtained. In an alternative case where film is utilized, the exposed film may be scanned to obtain a digital panoramic image.

In step S5, noise is removed from the image, and in step S6 the image is filtered using a low pass filter and then equalized in step S7, in accordance with panoramic x-ray imaging techniques known in the art. In step S8 the practitioner locates the phantom in the computer-generated image and, in step S9, the anatomic region of interest is identified. The anatomic region of interest could include the maxilla, mandible, or another oral structure. The region of interest can be identified through a variety of schemes including anatomic landmarks or structure and threshold-based segmentation algorithms. The sequence can be automatic and generated entirely by the computer or otherwise semi-automatic and thus require user intervention. The mental foramen, for instance, is a region of radiolucency typically located between the first and second premolar. This can be identified by the user or software can otherwise be programmed to locate the region.

A check is performed in step S10 to confirm that the phantom is positioned properly. In step S11 the computer software establishes the relationship between pixel value and density, and in step S12 the BMD of the patient calculated. It is noted that the BMD can be calculated since the pixel values of the spheres are known, and a specific region of interest is identified using the software and user intervention if desired. The BMD can be calculated fairly quickly, i.e. while the patient is in the clinician's office. The panoramic x-ray positioning routine described herein may be better suited for the computation of BMD, whereas another examination may be performed for general panoramic imaging applications.

As a person having ordinary skill in the art would readily appreciate, the present invention makes use of certain known techniques in computing bone mineral density, including those discussed in the Background of the Invention section, along with the novel features disclosed herein. For example, an exemplary embodiment of the present invention utilizes a panoramic x-ray system containing an x-ray tube capable of dual-energy assessment. Dual energy x-ray has the advantage of separating the density contributions of soft and hard tissue. As known in the art, the x-ray tube may contain k-edge filtering or may activate alternating pulses to create energy profiles appropriate for dual-energy-densitometry. Alternatively, the system could employ single-energy x-ray, as this technique is native to most panoramic x-ray systems. In one dual-energy embodiment, a DEXA algorithm is applied as described in U.S. Pat. No. 5,852,647 (Schick et al.), which is hereby incorporated by reference in its entirety.

As mentioned above, the reference phantom is constructed of materials that replicate the x-ray attenuation profile of the involved tissues and the x-ray attenuation characteristics of bone. Materials that have been used to replicate hard tissue (bones) include aluminum and hydroxyapatite. Soft tissue (skin, muscle, tendons, etc.) can be replicated with an epoxy or plastic. Of course, as would be understood by a person having ordinary skill in the art, in the single-energy embodiment only a hard tissue phantom would be necessary, since with the single-energy approach only the density of the region of interest is known and the soft and hard tissue can't be separated. On the other hand, in the dual-energy embodiment, a phantom containing both hard and soft tissue surrogates would be required; since it is known how the two x-ray energy levels project through those tissue types, then the simultaneous equations can be solved using a DEXA method such as disclosed in U.S. Pat. No. 5,852,647 (Schick et al.). In one embodiment, the reference phantom is a spherical soft tissue phantom made of materials such as certain plastics that are known to replicate attenuation as well. The aluminum balls would allow a single energy (SXA) technique to be utilized, whereas including a soft-tissue equivalent, a DXA technique can be utilized.

In a preferred embodiment a digital sensor is utilized since, as mentioned above, it has the benefit of being able to display an image instantaneously. Once the image is displayed, the computer software can generate quantitative densitometric information. Alternatively, with film or stored phosphor, the image would be digitized and then analyzed by a stand-alone computer and software.

The computer (e.g. 32 of FIG. 1) allows the user to control the operation of the system, and to view and analyze the dental images that the system creates. The computer 32 may be a conventional desktop, tower, laptop, or notebook computer, equipped with software for processing the data provided to it by the sensor. The computer may be connected to or have built in one or more input devices, such as a keyboard 36 and a mouse 38, and one or more output devices, such as a monitor 40 and a printer (not shown). These devices allow the user to control the operation of the system, and to view and analyze the dental images that the system creates through a graphical user interface. For example, an interface screen can enable users to easily access the information and initiate analysis. The computer might also include or be connected to a storage device (also not shown), such as a hard drive, for permanent storage of the images in patient files. Other potential storage devices include floppy disks, ZIP drives, magnetic tape, and optical medium such as CD-ROMS. A variety of computer program products comprising, in general, a computer-readable medium and the code necessary to calculate bone mineral density, can be used with the present invention.

The software might run on a PC-compatible, Macintosh, or Unix-based computer, among others. In one embodiment the software runs on a PC-compatible computer with a Pentium-based CPU running Windows 98, Me, 2000, or XP. Of course, this example is not meant to be limiting in any way, and the software could be written to be compatible with other or newer operating systems as well. In another embodiment, the software might be complementary to that used for acquiring intra-oral images, standard panoramic, video, and cephalometric examinations. The software would also preferably be compatible with dental practice management software.

The computer might contain at least 64 MB of RAM and 20 GB of hard disk space to store the software and image files. The display would preferably be optimized for video images at 800×600×24-bit color. It might also be advantageous to bundle the system with a photo-quality printer for printing examinations and a backup system for storing image and patient data.

As described herein, the present invention provides a system and method of computing oral BMD using a panoramic dental x-ray system and a reference standard. As noted, a panoramic dental x-ray system is ideally suited for this application since dental practitioners, implant specialists and the like typically have this equipment in their offices. The geometric design and the placement of the reference phantom are among the notable features of the present invention. Using a digital sensor, a preferred embodiment, can allow for quick display of the image and calculation of the bone mineral density through the software procedure. By virtue of the features of the present invention, more accurate BMD calculations can be achieved and the cost of performing such calculations can be reduced.

While the invention has been particularly shown and described with respect to preferred embodiments thereof, it will be understood by those skilled in the art that changes in form and details may be made therein without departing from the scope and spirit of the invention.

Having described the invention, what is claimed as new and secured by Letters Patent is:

1. A method of computing oral bone mineral density using a panoramic x-ray system, comprising the steps of:

providing a reference phantom having a known density;

obtaining a digital panoramic image of a body part and the reference phantom by revolving an x-ray generator and an opposing x-ray receiver through a plurality of angular positions that define a region of interest while emitting x-rays from the x-ray generator to irradiate the body part and the reference phantom at each of the plurality of angular positions, wherein the reference phantom is disposed in a location free from anatomical features and so as to irradiate the body part with substantially equal x-ray energy as the reference phantom for each of the plurality of angular positions, so that a relative measure of attenuation is ascertained for each of the plurality of angular positions;

for each of the plurality of angular positions, establishing a relationship between a region of the image corresponding to a portion of the body part and a region of the image corresponding to the reference phantom using the ascertained relative measure of attenuation; and calculating bone mineral density based upon the established relationships and the known density of the reference phantom.

2. The method as set forth in claim 1, in which said step of obtaining a digital panoramic image of a body part is accomplished utilizing a digital sensor.

3. The method as set forth in claim 1, in which said step of obtaining a digital panoramic image of a body part is accomplished by exposing film and scanning the film to obtain the digital panoramic image.

4. A method of computing oral bone mineral density using a panoramic x-ray system, comprising the steps of:

providing a reference phantom having a known density;

obtaining a digital panoramic image of a body part and the reference phantom by revolving an x-ray generator and an opposing x-ray receiver through a plurality of angular positions that define a region of interest while emitting x-rays from the x-ray generator to irradiate the body part and the reference phantom at each of the plurality of angular positions, wherein the reference phantom is disposed in a location free from anatomical features and so as with irradiate the body part to substantially equal x-ray energy as the reference phantom for each of the plurality of angular positions, so that a relative measure of attenuation is ascertained for each of the plurality of angular positions;

for each of the plurality of angular positions, establishing a relationship between the known density of the reference phantom and a region of the panoramic image corresponding to the reference phantom using the ascertained relative measure of attenuation; and applying the established relationships to a region of the panoramic image corresponding to at least a portion of the body part to calculate the bone mineral density of the body part.

5. The method as set forth in claim 4, in which said step of obtaining a digital panoramic image of a body part is accomplished utilizing a digital sensor.

6. The method as set forth in claim 4, in which said step of obtaining a digital panoramic image of a body part is accomplished by exposing film and scanning the film to obtain the digital panoramic image.

7. The method as set forth in claim 1, in which the reference phantom is spherical in shape.

\* \* \* \* \*